United States Patent [19]

Labianca

[11] 4,375,816

[45] Mar. 8, 1983

[54] CATHETERS FOR SHUNTING SYSTEMS FOR THE TREATMENT OF HYDROCEPHALUS

[76] Inventor: Michele Labianca, Via Gorizia 182, Turin, Italy

[21] Appl. No.: 190,777

[22] Filed: Sep. 25, 1980

[51] Int. Cl.³ .......................................... A61M 25/00
[52] U.S. Cl. ........................................ 604/8; 604/275
[58] Field of Search ............... 128/239, 214 R, 334 R, 128/334 L, 348–350 R

[56] References Cited

U.S. PATENT DOCUMENTS

| | | | |
|---|---|---|---|
| 1,899,781 | 2/1933 | Twiss | 128/350 R |
| 2,431,587 | 11/1947 | Schnee | 128/350 R |
| 3,233,610 | 2/1966 | Wade | 128/350 V |
| 3,298,372 | 1/1967 | Feinberg | 128/350 R |
| 3,503,079 | 3/1970 | Smith | 3/1.5 |
| 4,054,139 | 10/1977 | Crossley | 128/348 X |

OTHER PUBLICATIONS

Scarff–J. Neurol. Neurosurg. Psychiat–1963 #26–pp. 1–26.

Primary Examiner—Dalton L. Truluck
Attorney, Agent, or Firm—Sughrue, Mion, Zinn, Macpeak & Seas

[57] ABSTRACT

A shunting system for the treatment of hydrocephalus comprises a proximal catheter and/or a distal catheter in which a proximal and/or a distal end part of a tube of silicone rubber or other synthetic flexible polymer is constituted by a tip of titanium fixed to a corresponding end of the tube and affording an internal flow passage communicating at one end with flow apertures formed in the lateral walls of the tip and at the other end with the interior of the tube.

18 Claims, 5 Drawing Figures

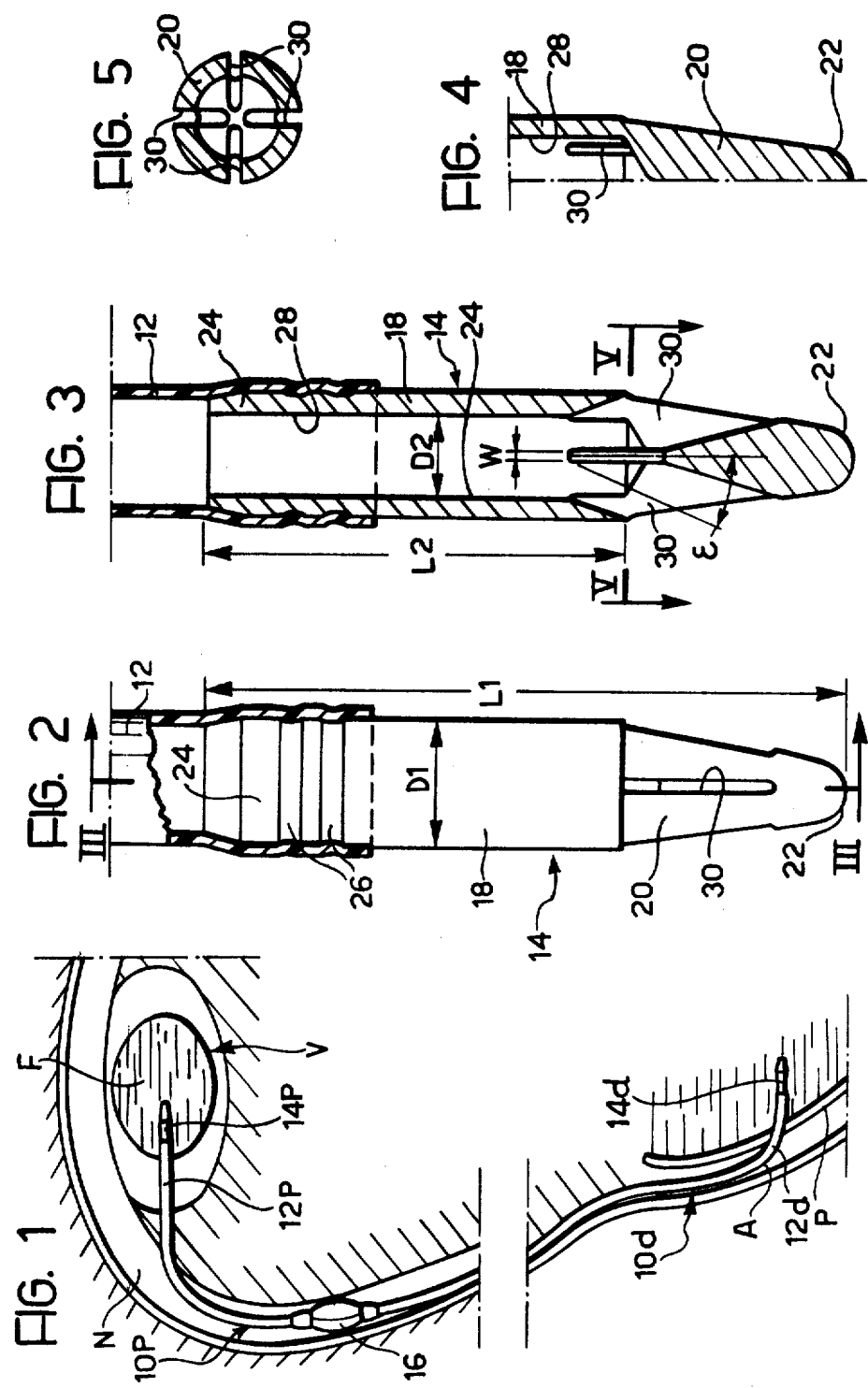

CATHETERS FOR SHUNTING SYSTEMS FOR THE TREATMENT OF HYDROCEPHALUS

BACKGROUND OF THE INVENTION

The present invention relates to shunting systems for cerebro-spinal fluid for use in treating hydrocephalus, commonly referred to as "shunting systems", and in particular relates to a catheter for such systems of the type comprising a tube of flexible synthetic polymer, such as silicone rubber, which is provided with a proximal end part for insertion in a cerebral ventricle and/or a distal end part for insertion in a body cavity, the end parts having flow apertures in their respective lateral walls for the flow of cerebro-spinal fluid from the ventricle into the tube and for the outflow of the said fluid from the tube into the body cavity.

The purpose of shunting systems for the treatment of hydrocephalus is to effect periodic drainage of excess cerebro-spinal fluid from the cerebral ventricle, normally ventricle III, in order to maintain the endrocranial tension or pressure at normal physiological values.

Such systems comprise a proximal catheter which consists essentially of a tube which generally runs from the ventricle to the mastoidal region and a proximal or ventricular end part which is inserted in the cerebral ventricle, passing through the foramen of Munro. The other end of this tube, situated in the mastoidal region, is generally connected to the inlet of a capsule, preferably subcutaneous, which acts both as an accumulator-reservoir for collecting the cerebro-spinal fluid drained from the ventricle, and as a pump, operable periodically by a manual compression applied through the skin to exhaust the accumulated fluid downstream.

The outlet of the capsule is connected to one end of a distal catheter consisting of a flexible tube similar to that previously mentioned and extending over a path which is at least partly subcutaneous. The other, distal, end of this latter catheter is inserted into a body cavity to afford a definitive drainage for the fluid. For the present the aforesaid cavity for the discharge of the fluid is the peritoneal cavity, the left cardiac auricle or a jugular vein. In hypersecretive hydrocephalus a shunt for the cerebro-spinal fluid may be provided in the subcutaneous tissue of the nucal region, in the retroperitoneal space, or in a ureter. Other shunting systems comprise a single catheter in the form of a continuous flexible tube which extends from the ventricle to the body cavity into which the fluid is to be discharged.

The catheters are preferably made of flexible silicone rubber tubing but may alternatively be made of other synthetic polymers which are biologically inert. The tubing used may have an internal and external diameter of the order, respectively, of 1.3 millimeters and 2.5 millimeters. The aforesaid capsule, if employed, is preferably of silicone rubber with a reinforcement of "dacron" or polypropylene.

In known shunting systems the aforesaid proximal and distal end parts are formed by the said silicone rubber tubing. These end parts have closed tapered ends and their lateral walls are provided with a multiplicity of small apertures in the form of holes for the ingress of fluid from the ventricle into the internal cavity of the tube or for the discharge of fluid from the internal cavity of the tube into the body cavity.

Shunting systems for hydrocephalus suffer from the severe disadvantage of blockage of the apertures and of the internal bore of the tube, after a certain period of use, frequently less than a year. Such blockage occurs in the proximal and distal end parts as a result of the deposition of filaments of fibrin. These deposits form predominantly on the external surfaces of the end parts.

Such blockages render the shunt system useless and necessitate frequent intervention if severe discomfort for the patient is to be avoided. Furthermore, the surgical intervention, in itself complex, necessary to remove the blockage or replace the shunt system is always attended by risks, and may even be fatal.

These disadvantages are the more acute when it is remembered that the greater part of cases of hydrocephalus occur in very young children and newly born babies.

The primary object of the present invention is to provide a catheter of the type previously referred to which avoids the disadvantages associated with blockage of the apertures and of the bore of the tube in its proximal and/or distal end parts.

SUMMARY OF THE INVENTION

According to the present invention the aforesaid problem is solved by means of a catheter of the type previously mentioned in which the said end parts or one of the said end parts is formed by a titanium tip fixed to a corresponding end of the tube and having an internal flow duct communicating at one end with the said flow passage and at the other end with the bore of the tube.

THEORY OF THE INVENTION

The theory on which the present invention is based will now be explained.

The cerebro-spinal fluid, in a normal subject, revealed the following composition when subjected to analysis, according to C. A. Keele and E. Neil:

| Constituent | Concentration |
| --- | --- |
|  | mg/100 cm$^3$ |
| Na$^+$ | 310 |
| HCO$_3^-$ | 1310 |
| Ca$^{++}$ | 5.3 |
| K$^+$ | 12.0 |
| HPO$_4^{--}$ | 1.8 |
| SO$_4^{--}$ | 0.6 |
| Glucose | 70 |
| Protein | 20–35 |

It will thus be noted that the fluid contains a high percentage of sodium and potassium, positively ionised. In the fluid these ions are combined in the form of dissolved halides, predominantly chlorides.

The concentration of the solution, already high in a normal subject, assumes a very high value in a patient suffering from hydrocephalus, as a result of the increased endocranial tension or pressure, which in acute cases may reach enormous values, of the order of $7 \times 10^5$ Pa, as compared with 650–130 Pa in a normal subject.

The halides are by their nature easily ionisable. It will therefore be appreciated that ideal conditions for the ionic dissociation of the halides of sodium and potassium exist in the cerebro-spinal fluid present in a cerebral ventricle of a patient suffering from hydrocephalus.

This dissociation is effectively enhanced to a high degree by the effect of the α particles present in the fluid. The accumulation of the α particles thus augments the concentration of the solution.

The material conventionally used in a ventricular catheter is a high polymer synthetic elastic material. A characteristic common to all synthetic elastic polymers is the presence, within the material, of electrostatic fields, due to covalent bonds shared between atoms of different electro-negativity.

The walls of a catheter of silicone rubber or other synthetic polymer are thus capable of exerting a strong attractive force on electro-positive particles, for example, sodium and potassium ions. The α particles present in the cerebro-spinal fluid collide with the molecules in solution within the proximal or distal end parts of a catheter and in their passage through these parts ionise the molecules. The resulting electro-positive ions accumulate on the external and internal surfaces of these end parts. There is consequently a high probability of the formation of occluding deposits of fibrin as a direct consequence of the phenomenon of electrophoresis between the ions and the material of the catheter.

Examination of catheters extracted from patients which have become blocked by deposits of fibrin has shown that these deposits are found largely on and within the above mentioned proximal and, to a lesser extent, distal end parts of such catheters.

Titanium is one of the transition elements in group IVb of the periodic classification, the atomic structure of which includes two unpaired electrons giving rise to non-compensated magnetic fields: in other words, titanium is a paramagnetic material, and exhibits a weak magnetic attraction.

From the electrical point of view, titanium may be considered to be neutral, as with any other atomic structure, since, in the absence of modifying external perturbations the centres of gravity of the nuclei and their surrounding electrons coincide, resulting in internal compensation of electrical charges of opposite polarity.

Titanium is thus a material which is not capable of exerting an attractive force on ions, and in particular on the electro-positive ions which are manifestly the cause of the occlusive deposits of fibrin referred to above.

The α particles which are present in the cerebro-spinal fluid and which give rise to the ionisation phenomena will dissipate their energy in a very short path, of the order of 1 centimeter. Consequently there will be no substantial ionisation downstream of the proximal end part and upstream of the distal end part of a catheter, since the α particles which are largely responsible for the ionisation will have expended their energy.

In definitive terms it is sufficient that titanium be present on at least the extreme proximal end part of the catheter and preferably also the distal end part, while the remaining part of the tube may be of a flexible synthetic polymer, and in particular silicone rubber, material which is known to be well suited to this purpose by virtue of its flexibility and its biological inertness.

The sole purpose of the titanium tips of the end parts is in fact to prevent occlusive depositions as a consequence of ionisation, which in turn is caused principally by the α particles, the tips being of a sufficient extent to ensure that the α particles exhaust their energy.

Titanium is also chosen because of its other advantageous property, which may be regarded as "conventional". In fact, the most important chemical property of titanium is its excellent resistance to chemical attack. Titanium is resistant to attack by corrosive agents, whether liquid or gas, which would otherwise give rise to oxidation, corrosion or indeed any other surface modification. This is of great significance, remembering that each of these effects may be enhanced considerably by the simultaneous action of intense biochemical activity to which the material of the catheter tip is subjected when located in an organ of a patient.

Titanium has a high resistance to corrosion, especially in the presence of chloride and in oxidising surroundings, since in such surroundings, at moderate temperatures such as body temperature, a superficial passivation occurs, resulting in a surface layer of oxide which protects the titanium from further chemical attack.

Titanium is also resistant to chlorine gas even when wet, to oxidising acids such as nitric acid and aqua regia, to sulphuric and hydrochloric acids of low concentrations, as well as to the majority of organic acids, at ambient temperature.

Dilute alkalis do not have any effect on titanium, which also has a high resistance to galvanic corrosion. Finally, titanium is detectable by X rays.

All the above characteristics therefore render the use of titanium ideal in a catheter or a shunting system.

Preferably the flow duct of the tip has a length between 1 and 1.5 centimeters. Lengths of this order are in fact sufficient to ensure that the α particles exhaust their energy within the limits of the flow conduit of the tip, without imposing upon the latter an excessive length.

The invention also comprehends a terminal element in the form of a tip of the aforesaid type, connectable to one end of a tube of flexible synthetic polymer for the manufacture of a catheter according to the said invention.

BRIEF DESCRIPTION OF THE DRAWINGS

Further characteristics of the invention will appear from the following description given by way of non-limiting example with reference to the accompanying drawings, in which:

FIG. 1 is a schematic representation of a ventricular-peritoneal shunting system according to one embodiment of the invention;

FIG. 2 is an elevational view of a terminal element of a catheter of the system of FIG. 1, coupled to the end of the flexible tube of a catheter, shown partially in longitudinal section;

FIG. 3 is a longitudinal section taken along the line III—III of FIG. 2;

FIG. 4 is a partial longitudinal section of one half of the terminal element, taken in a plane perpendicular to the plane of FIG. 3, and FIG. 5 is a transverse cross-section on the line V—V of FIG. 3.

DETAILED DESCRIPTION OF THE ILLUSTRATED EMBODIMENT

Referring to FIG. 1 a shunting system comprises a proximal catheter 10p and a distal catheter 10d. The proximal and distal catheters include respective flexible tubes 12p and 12d of silicone rubber. The proximal tube 12p is provided with a proximal terminal element 14p.

The proximal element is inserted in a cerebral ventricle (normally ventricle III), indicated by reference letter V, and allows the flow of cerebro-spinal fluid F into the proximal tube 12p. The latter follows a subcutaneous path in the nucal region N and is connected to a capsule 16 of known type, also located subcutaneously and situated in the mastoid region. The capsule 16 functions as an accumulator-reservoir for collecting the cerebro-spinal fluid delivered from the ventricle V, or as a pump operable periodically by manual compression applied through the skin.

The distal tube 10d extends from the capsule 16 and follows a subcutaneous path through the clavicular region, extending into the abdominal region A, where a distal terminal element 14d is provided. The latter is inserted through the peritoneum P into the peritoneal cavity, where the ventricular fluid flows through the terminal element 14d to be discharged into the peritoneal fluid.

FIG. 1 shows only one example of a shunting system to which the present invention is applicable. In other systems, the body cavity utilised for the discharge of the ventricular fluid and into which the distal terminal element 14d is inserted may be one of the cavities mentioned in the introductory part of the present specification. Similarly, the capsule 16 may be omitted and a unitary catheter may be used comprising a single tube provided, at its two ends, with proximal and distal terminal elements respectively.

The proximal and distal terminal elements 14p and 14d are preferably identical. Their configuration will be described with reference to FIGS. 2-5, in which the terminal element is indicated generally by reference numeral 14. The associated tube, indicated by reference numeral 12, represents either the proximal tube 12p or the distal tube 12d of FIG. 1, or alternatively a single continuous tube interconnecting a pair of the said terminal elements 14.

The terminal element 14 comprises a tip made of a single piece of technically pure titanium. The tip is an elongate body comprising successively a substantially cylindrical tubular portion 18 and a substantially conical free end portion 20, terminating in a rounded apex 22. The apex 22 is designed to penetrate, during the implantation operation, either the cerebral ventricle V or the body cavity used for discharge of cerebro-spinal fluid, such as the peritoneal cavity.

The tubular portion 18 of the tip 14 has a connection end 24 the external cylindrical surface of which is formed with two circumferential grooves 26. The connection end 24 is inserted into the corresponding end of the flexible silicone rubber tube 12. The connection between the end 24 and the cooperating end of the tube 12 is effected by force accompanied by heating or by effecting a pre-heating of the end of the tube 12 such as to soften it sufficiently to permit the insertion of the connection end 24. Subsequent cooling results in a consolidated secure connection between the two ends, by virtue of the contraction of the silicone rubber which enters into the grooves 26.

A coaxial cylindrical bore 28 extends through the tip 14 from the end which is inserted into the tube 12, the bore 28 extending as far as a transition zone between the cylindrical portions 18 and the conical portion 20. The lateral walls of the conical portion 20 are formed with four slit-like apertures 30 which afford communication between the exterior of the terminal element 14 and the adjacent end of the bore 28, which constitutes a flow duct.

In a proximal terminal element such as that indicated by 14e the apertures 30 would serve for the flow of cerebro-spinal fluid from the cerebral ventricle V into the bore 28, which acts a flow duct and which opens into the interior of the tube 12 (12p in FIG. 1).

In a distal terminal element such as that indicated by reference numeral 14d the cerebro-spinal fluid which flows from the tube 12 (12d in FIG. 1) flows along the bore 28 and is discharged into the body cavity through the slit-like apertures 30.

The apertures 30 are rectangular in cross-section, with parallel walls, the apertures being elongate in the longitudinal direction of the tip 14. The apertures 30 converge towards the axis of the flow duct 28 in the direction of the connection end 24 of the terminal element 14 which is connected to the tube 12.

The four slit-like apertures 30 are arranged in two pairs, with diametrically opposite pairs disposed in respective diametral medial planes which are perpendicular to each other.

The aforesaid convergence of the apertures favours either the flow of cerebro-spinal fluid into the bore 28, or the outflow of the cerebro-spinal fluid from the bore 28 into the receiving body cavity, according to whether the terminal element 14 is a proximal or distal element respectively.

Whether the terminal element is used as a proximal or distal element, the angle of convergence of the slit-like flow apertures 30 with respect to the longitudinal axis of the flow duct 28 should preferably be as small as possible so as to direct the flow of fluid which passes through the apertures 30 as near as possible in a direction parallel to the axis of the flow duct 28. In the case of a proximal terminal element the flow of cerebro-spinal fluid which enters the flow duct has a regular laminar flow, substantially without vortices, or with negligible vortices only over the wall of the duct 28. In the case of a distal terminal element the said disposition favours a significant spreading of the four currents of fluid discharged from the apertures, before these form vortices in the vicinity of the mouths of the said apertures.

The reasons for using a titanium tip have already been explained in the introductory part of the present specification. The object is to tend to eliminate altogether vortices within the terminal element 14, or to make the vortices occur as far as possible from the terminal element, since the presence of vortices may extend the ionic activity, impeding discharge through or completely blocking the element 14, contrary to what is desired.

It may appear to be more advantageous to effect direct communication between the flow duct 28 and the exterior of the terminal element or tip 14 through the apex 22 rather than through the lateral apertures 30. Such an arrangement would, however, suffer from the disadvantage that in the operation of inserting the tip into the ventricle or into the body cavity for discharge, the mouth of the duct 28 at the apex 22 would, as it were, act as a punch which could lead to the occlusion of the duct by pieces of tissue.

On the other hand, the minimal angle of convergence of the slit-like apertures 30 is dictated by a simple technological reason: the apertures 30 are preferably formed by means of electro-erosion and it is not possible by this method of formation to form apertures with excessive angles with respect to the axis of the flow duct 28, which coincides with the axis of the terminal element 14. The angles of convergence of the slit-like apertures 30 should in fact have the optimum values specified below.

Another factor which contributes to a regular flow within the flow duct 28, especially in the case of a proximal terminal element, is the arrangement of the slit-like apertures in two opposed pairs. It would be possible to use a single pair of apertures or more than two pairs of apertures, but the adoption of two pairs of apertures disposed in a cruciform arrangement is in practice an optimum configuration since it permits an overall optimum flow cross-section, given the small dimensions of the terminal element 14, which may typically be as specified below, without employing apertures too narrow or too large and without having apertures of excessive length.

The principal dimensions of an optimum terminal element 14 for connection to a tube of silicone rubber having an internal diameter of 1.8 millimeters and an external diameter of 3 millimeters are set out below for a typical practical embodiment.

Total length $L_1$ of terminal element 14: about 15.5 mm
Length $L_2$ of flow duct 28 and of cylindrical portion 18: 10 mm
External diameter $D_1$ of cylindrical portion 18: 3 mm
Diameter $D_2$ of flow duct 28: 2 mm
Width W of each slit-like aperture 30: 0.3 mm
Total transverse cross-sectional area of the four apertures 30: about 2 $mm^2$
Vertex angle of conical portion 20: 30°
Angle $\epsilon$ formed between the axis of the terminal element and the mean direction of convergence of the slit-like apertures 30: 17.5°

As regards the lengths $L_1$ $L_2$, the length $L_2$ of the flow duct 28 is chosen to be equal to at least 1 centimeter and may amount to 1.5 cm so as to ensure, as explained in the introductory part of the present specification, the dissipation of the energy of the $\alpha$ particles in the titanium portion of the tip. On the other hand, the length $L_2$ determines essentially the total length $L_1$ of the tip 14, and this length should not exceed 2 centimeters. In fact it is imperative that a tip inserted in a small cavity, such as a ventricle, be contained completely within the cavity and that it be supported elastically by the end of the flexible tube, so as to avoid breaking the connection by the effect of pulsatile phenomena.

The total cross-section of about 2 $mm^2$ of the four apertures 30 is chosen so as to be substantially equal to the overall cross-section of the lateral flow passages of the ends of the silicone rubber tube employed in the prior art, which form this point of view are found to be satisfactory. The width W of 0.3 mm of the apertures is chosen in order that the longitudinal dimensions of the apertures are such as to form the mouth in the conical end portion 20, with a length which is not excessive, so as to avoid imposing a total length $L_1$ which is also excessive. Moreover, with this dimensioning the edges of the apertures 30 are spaced somewhat rearwardly with respect to the apex 22 (by a distance of the order of 1.7 mm.). This assists in preventing the picking up of fragments of tissue by the apertures 30 as the tip 14 passes through the walls of the cavity into which the terminal element is to be inserted.

Finally, a mean angle of convergence $\epsilon$ of the slit-like apertures of the order of 17.5° and a vertex angle of the conical end portion of the order of 30° together constitute a good compromise between the small angle of convergence desirable for the apertures 30, the need to facilitate the formation of the said apertures, and the optimisation of the conical portion 22. It may be possible to increase the said vertex angle, for example to 35°, in order obtain a smaller angle $\epsilon$ of convergence of for example 15°, or to reduce the vertex angle, for example to 25°, accepting a greater angle $\epsilon$ of convergence of, for example 25°, without the increased vertex angle leading to the formation of unwanted vortices.

I claim:

1. A catheter for shunting systems for the treatment of hydrocephalus of the type comprising a tube of flexible synthetic polymer, a proximal end part of said tube adapted for insertion into a cerebral ventricle, a distal end part of said tube adapted to be inserted into a body cavity, and apertured portions in said end parts defining flow passages in their respective lateral walls for the flow of cerebro-spinal fluid from the ventricle into the tube and for the flow of said fluid from the said tube into said body cavity, wherein at least one of said end parts is constituted by a terminal element of titanium to prevent occlusive deposits of fibrin as a consequence of the ionization of said fluid by $\alpha$ particles present in said fluid, said terminal element being fixed at one end to said flexible tube and having at its other end lateral walls formed with said apertured portions and an internal flow duct communicating with said apertures and with the interior of said tube.

2. Catheter as defined in claim 1 wherein the flow duct of the terminal element has a length between 1 and 1.5 centimeters.

3. Catheter as defined in claim 1 or claim 2 wherein said at least one terminal element comprises, in succession, a substantially cylindrical tubular portion connected to the flexible tube and formed with a coaxial cylindrical bore constituting the said flow duct and a substantially conical free end portion having a rounded apex, the said apertures being formed in said free end portion and defining passages extending through the lateral walls of said portion.

4. Catheter as defined in claim 1 or claim 2 wherein the flow-passage defining apertures are in the form of narrow rectilinear slits with parallel walls which are elongate in the direction of the longitudinal axis of the respective terminal element.

5. Catheter as defined in claim 4 wherein the slits converge towards the axis of the flow duct and towards the end of the terminal element which is connected to the flexible tube.

6. Catheter as defined in claim 5 wherein the terminal element has at least one pair of said slits diametrically opposed and disposed in a common median plane.

7. Catheter as defined in claim 5 wherein the terminal element has two pairs of said slits diametrically opposed in respective pairs, the two pairs of slits lying in respective common diametral median planes which are perpendicular to each other.

8. Catheter as defined in claim 5 or claim 6 wherein each slit has a mean direction of convergence defining, with the longitudinal axis of the terminal element, an angle between 15° and 20° and wherein the conical end portion has a vertex angle between 25° and 35°.

9. Catheter as defined in claim 3, wherein the tubular portion of the terminal element has an end part adapted for connection to the flexible tube and formed in its external surface with circumferential grooves, said end part being force-fitted with heat into the corresponding end of the flexible tube of synthetic polymer.

10. Terminal element connectable to one end of a tube of synthetic flexible polymer such as silicon rubber, to form, in combination with said tube a proximal or distal end portion of a catheter for a shunting system for the treatment of hydrocephalus, wherein said terminal element is formed of titanium to prevent occlusive deposits of fibrin from cerebro-spinal fluid as a consequence of the ionization of said fluid by α particles present in said fluid, said terminal element having an internal flow duct communicating at one end with apertures in the lateral walls of said terminal element and being open at its other end for communication with the interior of the flexible tube.

11. Terminal element as defined in claim 10 wherein the flow duct has a length between 1 and 1.5 centimeters.

12. Terminal element as defined in claim 10 or claim 11 comprising, in succession from the said other end connectable to the flexible tube, a tubular, substantially cylindrical portion formed with a cylindrical coaxial bore constituting the said flow duct and a substantially conical free end portion having a rounded apex, the said apertures being formed in and extending through the lateral walls of the said conical free end portion.

13. Terminal element as defined in claim 10 or claim 11 wherein the said apertures are in the form of rectilinear slits with flat parallel sides elongate in the longitudinal direction of the terminal element.

14. Terminal element as defined in claim 13 wherein the flow passages defined by the slits converge towards the axis of the internal flow duct and towards the said other end which is connectable to the flexible tube.

15. Terminal element as defined in claim 14 including at least one said pair of slits diametrically opposed and disposed in a common diametral median plane.

16. Terminal element as defined in claim 14 having two said pairs of slits which are diametrically opposed in respective pairs, the two pairs of slits being disposed in respective common diametral planes which are perpendicular to each other.

17. Terminal element as defined in claim 14, claim 15 or claim 16 wherein each of the said slits has a mean direction of convergence forming with the axis of the terminal element an angle between 15° and 25° and wherein the conical free end portion has a vertex angle between 25° and 35°.

18. Terminal element as defined in claim 12, wherein the substantially cylindrical tubular portion has a connection end adapted to be inserted into the corresponding end of the tube of synthetic polymer, the external surface of said connection end being formed with circumferential grooves.

* * * * *